US005770449A

United States Patent [19]
Eccles et al.

[11] Patent Number: 5,770,449
[45] Date of Patent: Jun. 23, 1998

[54] VECTOR FOR INTEGRATION SITE INDEPENDENT GENE EXPRESSION IN MAMMALIAN HOST CELLS WHICH PERMIT IMMUNOGLOBULIN GENE EXPRESSION

[75] Inventors: Sarah Jane Eccles; Franklin Gerardus Grosveld, both of London, United Kingdom

[73] Assignee: Medical Research Council Ltd., London, United Kingdom

[21] Appl. No.: 483,999

[22] Filed: Jun. 7, 1995

Related U.S. Application Data

[62] Division of Ser. No. 402,880, Mar. 1, 1995, abandoned, which is a continuation of Ser. No. 173,954, Dec. 28, 1993, abandoned, which is a continuation of Ser. No. 953,772, Sep. 30, 1992, abandoned, which is a continuation of Ser. No. 768,942, Oct. 22, 1991, abandoned.

[30] Foreign Application Priority Data

Feb. 22, 1989 [GB] United Kingdom ............ 8904009

[51] Int. Cl.$^6$ .................... C12N 5/10; C12N 15/13; C12N 15/67; C12N 15/85
[52] U.S. Cl. ................. 435/375; 435/69.1; 435/70.3; 435/70.4; 435/172.1; 435/172.3; 435/320.1; 800/2; 514/44
[58] Field of Search .................. 514/44; 435/69.1, 435/70.1, 70.4, 91.4, 172.3, 320.1, 325, 326, 354, 355, 366, 372.2; 935/6, 36; 800/2, DIG. 1, DIG. 2; 536/24.1

[56] References Cited

PUBLICATIONS

I. Weissman et al. Scientific American 269 (3) (Sep. '94) 65–71.
G. van Assendelft et al. Cell 56 (Mar. 24, 1989) 969–77.
A. Hienhuis et al. Cancer 67 ('91) 2700–4.
N. Sutkowski et al. P.N.A.S. 91 (Sep. '94) 8875–9.
J. Sharpe et al. P.N.A.S. 90 (Dec. '93) 11262–6.
L. Madisen et al. Genes & Development 8 ('94) 2212–26.
D. Talbot et al. Nature 338:352–5 ('89).
K. Mercola et al. Science 208:1033–5 (80).
M. Clive et al. Nature 284 422–5 ('80).
Antoniou et al., "β–Globin dominant control region interacts differently with distal and proximal promoter Elements", Genes & Develolpment 4:1007–1013 (1990).
Brinster et al., "Introns increase transcriptional efficiency in transgenic mice", Proc. Natl. Acad. Sci. USA, vol. 85, pp. 836–840. (Feb. 1988).
Carson et al., "A linkage map of the mouse immunoglobulin lambda light chain locus", Immunogenetics, 29:173–179, (1989).
Greaves et al., "Human CD2 3'–Flanking Sequences Confer High–Level, T Cell–Specific, Position–Independent Gene Expression in Transgenic Mice", Cell, vol. 56, pp. 979–986, (Mar. 24, 1989).

Grosveld et al., "Position–Independent, High–Level Expression of the Human β–Globin Gene in Transgenic Mice", Cell, vol. 51, 975–985, (Dec. 24, 1987).
Hesse et al., "Regulated gene expression in transfected primary chicken erythrocytes", Proc. Natl., Acad. Sci. USA, vol. 83, pp. 4312–4316, (Jun. 1986).
Lang et al., "The structure of the human CD2 gene and its expression in transgenic mice", The EMBO Journal, vol. 7, No. 6, pp. 1675–1682, (1988).
Le thi Bich–Thuy et al., "An enhancer associated with the mouse immunoglobulin λ1 gene is specific for λlight chain producing cells," Nucleic Acids Research, vol. 17, No. 13, pp. 5307–5321, (1989).
Maniatis et al., "Regulation of Inducible and Tissue–Specific Gene Expression", Science, vol. 236, (Jun. 5, 1987).
McDougall et al., "A transcriptional Enhancer 3'$C_{\beta 2}$ in the T Cell Receptor β Locus", Science, vol. 241, p. 205–208, (Jul. 8, 1988).
Palmiter et al., "Dramatic growth of mice that develop from eggs microinjected with metallothionein–growth hormone fusion genes", Nature, vol. 300, (Dec. 16, 1982).

(List continued on next page.)

*Primary Examiner*—Charles C. P. Rories
*Attorney, Agent, or Firm*—Banner & Witcoff

[57] ABSTRACT

A vector for the integration of a gene into the genetic material of a mammalian host cell such that the gene may be expressed by the host cell. The vector comprises a promoter and the gene and in an immunoglobulin dominant control region derived from the mouse λ immunoglobulin gene locus capable of eliciting host cell-type restricted, integration site independent, copy number dependent expression of said gene. The DNaseI super hypersensitive site exemplified are i) about 2.35 kb upstream of the CAP site of the rearranged $\lambda_1$ gene, ii) about 2.5 kb upstream of the genomic V$\lambda_2$ segment or iii) about 30 kb downstream of the rearranged $\lambda_1$ gene. Mammalian host cells transformed with the vector are disclosed as are transgenic mammals transformed with the vector and a method of producing a polypeptide comprising culturing a transformed mammalian cell. A method of gene therapy comprising the steps of i) removing stem cells from the body of a mammal, ii) optionally killing stem cells remaining in the body, iii) transforming the removed stem cells with the vector containing a gene deficient or absent in the body, and iv) replacing the transformed stem cells in the body is also disclosed. Also disclosed is functional mouse immunoglobulin $\lambda_1$ enhancer consisting of a DNA sequence comprising all or a functional part of the DNA sequence between the EcoRI site 3.8 kb downstream of the Xho I site in the rearranged mouse $\lambda_1$ gene and the SnaBI site 10 kb downstream of this Xho I site. The functional mouse immunoglobulin $\lambda_1$ enhancer may comprise all or a functional part of i) the 1.3 kb first HindIII to HindIII DNA fragment downstream of the EcoRI site 3.8 kb downstream of the Xho I site in the rearranged mouse $\lambda_1$ gene, ii) the 3.3 kb HindIII to HindIII DNA fragment downstream of the EcoRI site 3.8 kb downstream of the Xho I site in the rearranged mouse $\lambda_1$ gene and spanning the SnaBI site 10 kb downstream of this Xho I site.

11 Claims, 13 Drawing Sheets

OTHER PUBLICATIONS

Picard et al., "A lymphocyte–specific enhancer in the mouse immunoglobulin K gene", Nature, vol. 307, pp. 80–82, (Jan. 5, 1985).

Stief et al., "A Nuclear DNA attachment element mediates elevated and position–independent gene activity", Nature, vol. 341, (Sep. 28, 1989).

Storb et al., "High expression of cloned immunoglobulin K gene in transgenic mice is restricted to B lymphocytes", Nature, vol. 310, pp. 238–241, (Jul. 19, 1994).

DNaseI fadeouts on J558L nuclei. DNA cut with A SphI and B SphI - XhoI
Blots were probed with Vλ₁ probe.

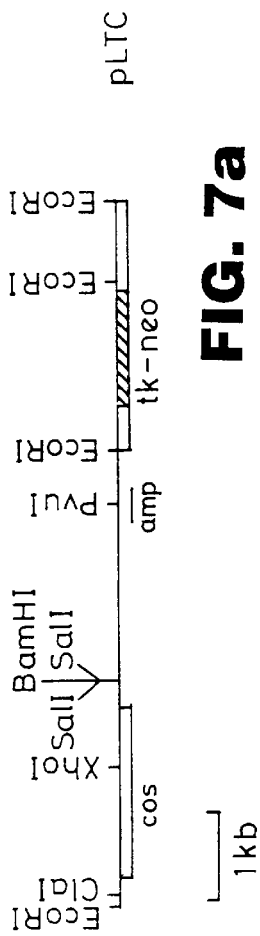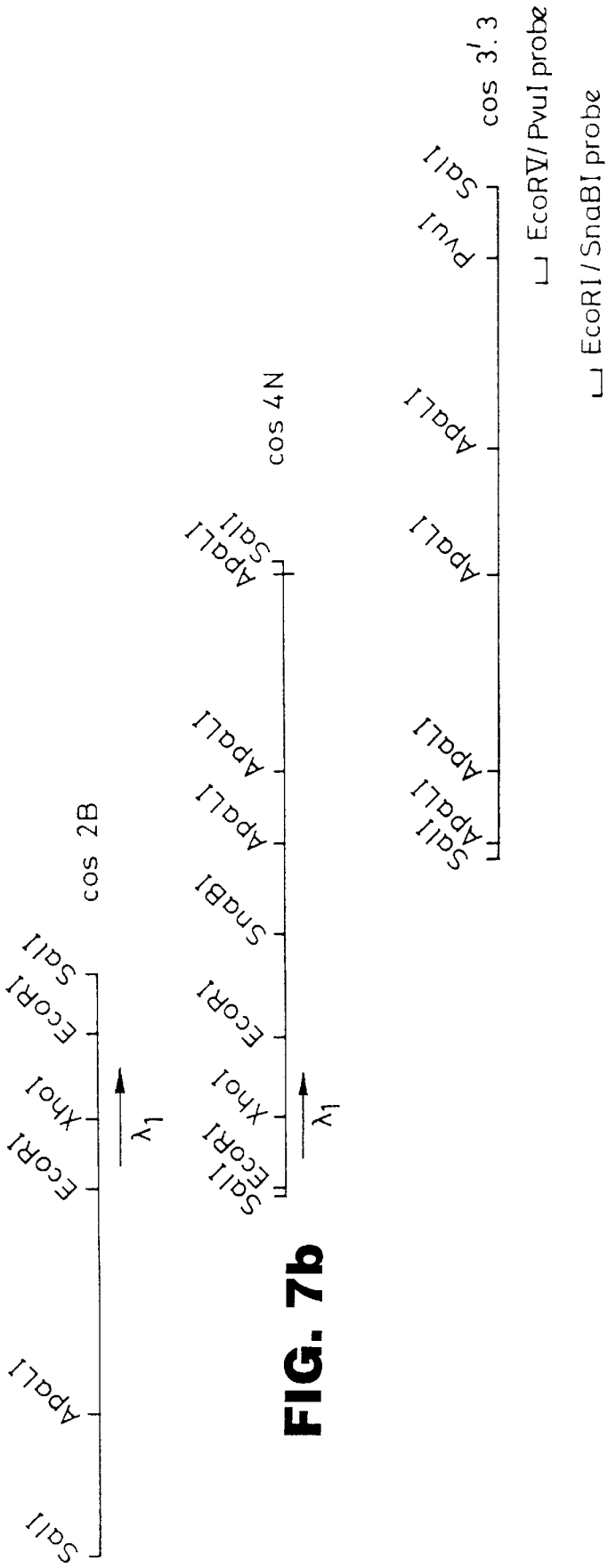
FIG. 7a
FIG. 7b

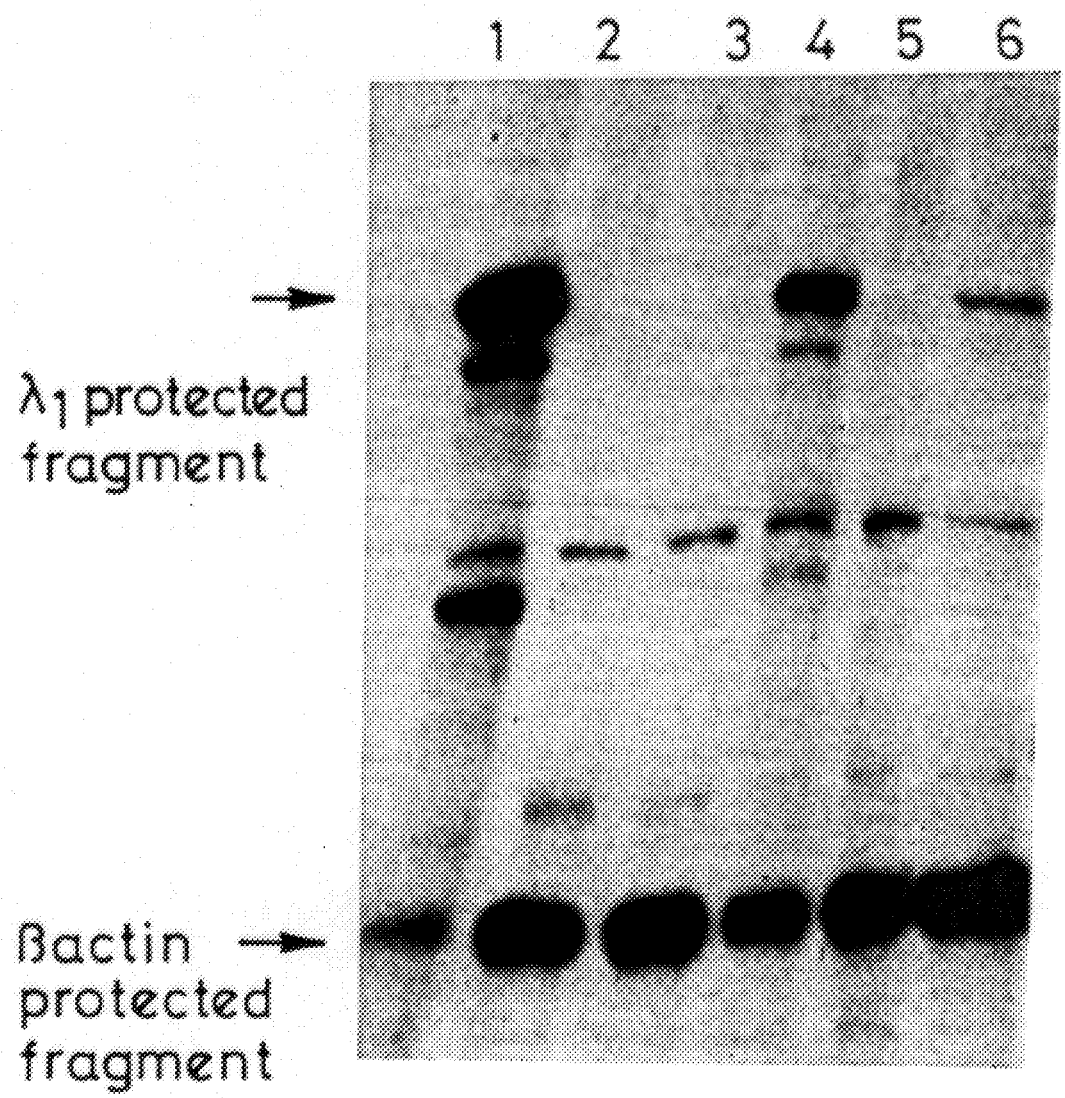

VECTOR FOR INTEGRATION SITE INDEPENDENT GENE EXPRESSION IN MAMMALIAN HOST CELLS WHICH PERMIT IMMUNOGLOBULIN GENE EXPRESSION

This application is a division of application Ser. No. 08/402,880, filed Mar. 1, 1995, now abandoned, which is continuation application of U.S. application Ser. No. 08/173,954, filed Dec. 28, 1993, now abandoned, which is a continuation application of U.S. application Ser. No. 07/953,772, filed Sep. 30, 1992, now abandoned, which is a continuation application of U.S. application Ser. No. 07/768,942 filed Oct. 22, 1991, now abandoned.

FIELD OF THE INVENTION

The present invention relates to recombinant DNA technology and in particular to a vector useful for transfecting mammalian cells in vivo and in vitro to obtain expression of a desired structural gene. The invention relation also to the use of such vectors in gene therapy and heterologous gene expression.

BACKGROUND TO THE INVENTION

There is a continuing need for improved expression vectors exhibiting high levels of expression. In particular, expression vectors for use in mammalian cell lines are of increasing importance both for the industrial production of desired polypeptides and for the development of therapies for genetic disorders.

There are many known examples of characterised structural genes, which together with appropriate control sequences may be inserted into suitable vectors and used to transform host cells. A significant problem with the integration of such a structural gene and control regions into the genome of a mammalian cell is that expression has been shown to be highly dependent upon the position of the inserted sequence in the genome. This results in a wide variation in the expression level and only very rarely in a high expression level. The problem of integration site dependence is solved by the present invention and arises from the discovery of specific sequences referred to herein as dominant control regions (DCRs) derived from immunoglobulin genes which have the property of conferring a cell-type restricted, integration site independent, copy number dependent expression characteristic on a linked gene system.

Two mammalian gene systems have been shown to possess DCRs, namely the β-like globin genes (Grosveld, F. G. et al, Cell, 51, (1987), 975; International patent application PCT/GB 88/00655), and the human CD2 T-cell marker gene (Lang, G., et al, EMBO J, 7, (1988), 1675; International patent application PCT/GB 88/00655).

When a mammalian gene such as β-globin containing all the usual control regions is introduced into transgenic mice, the gene is not expressed at the same level as the mouse β-globin gene and exhibits integration site position effects. This is characterized by a highly variable expression of the transgene that is not correlated with the copy number of the injected gene in the mouse genome. The same phenomenon has been observed in almost all the genes that have been studied in transgenic mice (Palmiter et al, Ann. Rev. Genet., (1986), 20, 465–499). Moreover, the level of expression of each injected gene in the case of β-globin is, at best, an order of magnitude below that of the endogenous mouse gene (Magram et al., Nature, (1985), 315, 338–340; Townes et al., EMBO J., (1985), 4 1715–1723; Kollias et al, Cell, (1986),46, 89–94). A similar problem is observed when the β-globin or other genes are introduced into cultured cells by transfection or retroviral infection. This poses a big problem when considering gene therapy by gene addition in stem cells. It is also a major problem for the expression of recombinant DNA products in cultured cells. Extensive screening for highly producing clones is necessary to identify cell-lines in which the vector is optimally expressed and selection for vector amplification or use of multicopy viral vectors is generally required to achieve expression levels comparable to those of the naturally occurring genes, such as for example β-globin genes in erythroleukaemic cell-lines.

In a chromosome, the genetic material is packaged into a DNA/protein complex called chromatin, one effect of which may be to limit the availability of DNA for functional purposes. It has been established that many gene systems (including the β-globin system) possess so-called DNaseI hypersensitive sites. Such sites represent putative regulatory regions, where the normal chromatin structure is altered, for instance by interaction with regulatory proteins or to allow such interaction.

Regions flanking the β-like globin gene locus which contain a number of "super" hypersensitive sites have been identified. These sites are more sensitive to DNase I digestion in nuclei than the sites found in and around the individual genes when they are expressed (Tuan et al PNAS USA, (1985), 80, 7551–7555). In addition, they are erythroid cell specific and they are present when any one of the globin genes is expressed.

Tuan et al describe the broad mapping of four major DNase I hypersensitive sites in the 5' boundary area of the "β-like" globin gene. The authors note that certain sequence features of these sites are also found in many transcriptional enhancers and suggest that the sites might also possess enhancer functions and be recognised by erythroid specific cellular factors.

It has been discovered that the complete β-globin gene with intact 5' and 3' boundary regions does not exhibit an integration site position dependence (see copending International patent application PCT/GB 88/00655). The regions of the locus responsible for this significant characteristic have been determined and shown to be associated with DNase I super hypersensitive sites. These dominant control regions are quite distinct from enhancers, exhibiting properties such as integration site independence not exhibited by the known enhancers. The dominant control region used in conjunction with the known promoter/enhancer element reconstitute the full transcription rate of the natural gene.

Immunoglobulin genes have been extensively studied in order to identify sequences regulating gene expression. An immunoglobulin molecule consists of two identical heavy polypeptide chains and two identical light polypeptide chains. The light chains may be either of the κ or λ type. The genes encoding the heavy chain, the κ light chain and the λ light chain are each located on separate chromosomes in the mouse and man.

Unlike most genes which are transcribed from continuous genomic DNA sequences, immunoglobulin genes are assembled from gene segments which may be widely separated in the germ line.

Functionally, heavy chain genes are formed by recombination of three genomic segments encoding the variable (V), diversity (D) and joining (J)/constant (C) regions of the molecule (FIG. 1). Functional light chain genes are formed by joining of two segments, one encoding the V region and the other the J/C region. Both the heavy chain and κ light chain loci contain many V gene segments (estimates vary between 100 s and 100 s) estimated to span approximately 300 kb on chromosome 16 in the mouse. It consists of four joining/constant region gene segments and two variable gene segments (FIG. 1). Recombination resulting in functional genes occurs predominantly between $V_1$ and either $J_1/C_1$ or $J_3/C_3$ elements or between $V_2$ and $J_2/C_2$ elements ($J_4/C_4$ is a pseudogene) although recombinations between $V_2$ and $J_3/C_3$ or $J_1/C_1$ are seen very rarely.

Control of transcription of both rearranged heavy and κ light chain genes depends both on the activity of a tissue specific promoter upstream of the V region (Mason, J. O. et al., Cell, (1985), 41, 479; Bergman, Y. et al., PNAS USA, (1984), 81, 7041) and a tissue specific enhancer located in the J-C intron (Gillies, S. D. et al., Cell, (1983), 33, 717; Banerji, J. et al., Cell, (1983), 33, 729; Picard, D. et al, Nature, 307, 80). These elements act synergistically (Garcia, J. V. et al., Nature, (1986), 322, 383). Recently a second B-cell specific enhancer has been identified in the κ light chain locus (Meyer, K. B. et al., EMBO J., (1989), 8, No. 7,1959–1964). This further enhancer is located 9 kb downstream of $C_k$.

More recently Bich-Thuy and Queen (1989 NAR 17:5307) described in enhancer activity immediately downstream of the rearranged $\lambda_1$ gene. Sequences downstream of the $\lambda_1$ gene increased expression of a chloramphenicol acetyl transferase (CAT) reporter gene linked to the $\lambda_1$ promoter in a myeloma cell line which made lambda light chains (J558L) but not in two myeloma cell lines which make κ light chains.

This enhancer activity differs in several ways from that of the heavy chain and κ light chain enhancers. Firstly, it displayed a marked orientation preference. Secondly, it consists of several segments which can independently stimulate transcription and which are spread over about 4 kb of DNA immediately downstream of the $\lambda_1$ coding sequence. Thirdly, it is apparently only expressed in λ chain producing myeloma cells and not in cells producing κ light chains.

Spandidos and Anderson (1984 FEBS Lett. 175:152) describe an 8 kb fragment (containing 2 constant region gene segments) from the human λ locus which increases the number of G418 resistant colonies obtained after transfection of myeloma cells with a plasmid containing the 8 kb fragment linked to the aminoglycoside-phosphotransferase (aph) gene under the control of an ε-globin promoter. Levels of aph specific mRNA were reported to be increased following transient transfection of this construct when compared with a construct lacking the 8 kb sequence. However, no controls were presented for transfection efficiency in the transient assays and no further reports relating to enhancer activity in the human λ locus have been published.

DNA fragments carrying rearranged heavy or κ light chain genes are expressed when transfected into lymphoid cells although generally at least 10 times less efficiently than endogenous immunoglobulin genes (Oi, V. T. et al., PNAS USA, (1983), 80, 825; Neuberger, M. S., EMBO J., (1983), 2, 1373). Expression of a similar DNA fragment containing a rearranged λ1 gene however is not detectable in transfected lymphoid cells and expression is only observed when an SV40 enhancer is added (Picard, D. et al., Nature, (1984), 307, 80; Cone, R. D. et al., Science, (1987), 236, 954). This is apparently due to the absence of a functional enhancer such as that present in the J-C introl on the κ gene.

Although promoter and enhancer elements associated with κ and heavy chain genes are sufficient to confer lymphoid cell specific expression of antibody genes, the level of expression is reduced compared with expression of endogenous antibody genes and genes are subject to position effects such that no clear relation exists between the level of expression and the copy number of the introduced gene (Oi, V. T. et al., PNAS USA, (1983), 80, 825; Neuberger, M. S., EMBO J., (1983), 2, 1373). Similar results are obtained when κ and heavy chain genes are introduced into transgenic mice (Storb U., et al., Ann. Rev. Immunol., 5, (1987), 151).

Sequences required for full regulation of antibody gene expression are therefore lacking from constructs used to date in expression studies (Grosschedl, R. et al., Cell, (1985), 55, 645).

We have no identified super hypersensitive sites in the rearranged $\lambda_1$ mouse immunoglobulin gene outside of the region previously suggested to be involved in expression of the $\lambda_1$ gene. The strong implication of our finding is that immunoglobulin gene expression shares a common feature with β-globin and CD2 expression, namely the existence of dominant control regions.

Many active genes have hypersensitive sites associated with their promoters. For example, a tissue specific DNaseI hypersensitive site is observed 300 bp upstream from the start of the coding region of the rearranged κ immunoglobulin gene (Chung, S-Y et al., PNAS USA, 80, 2427). No such site was identified in the rearranged $\lambda_1$ gene which was studies in the present work nor was any site identified in the J-C intron where hypersensitive sites associated with immunoglobulin enhancers have been identified in both the heavy chain (Mills, F. et al., (1984), Nature, 306, 807) and κ light chain genes (Chung, S-Y et al., PNAS USA, 80, 2427; Parslow, T. G. et al., NAR, (1983), 11, 4775; Weischet et al., NAR, (1982), 10, 3627).

The hypersensitive sites characteristic of the dominant control regions of the β-globin locus identified by Grosveld et al (Grosveld, F. G. et al., Cell, (1987), 51, 957–985) are referred to as "super hypersensitive". The designation "super" hypersensitive refers to the fact that these sites are much more sensitive to DNaseI that the "normal" hypersensitive site associated with the β-globin promoter (Groudine, M. et al., PNAS USA, (1983), 80, 7551). In the mouse λ locus, promoter hypersensitive sites are not detectable and the only DNaseI hypersensitive sites which are seen, map at larger distances from the gene.

The hypersensitive sites in the mouse λ locus indicate locations of sequences which, according to the present invention confer dominant control of immunoglobulin genes. On the basis of this mapping, DNA sequences flanking the rearranged gene in J558L have been closed.

The present invention is applicable to the production of transgenic animals and the techniques for producing such are now widely known. For a review, see Jaenisch, Science, (1988), 240, 1468–1474.

The present invention provides a solution to the problem of integration site dependence of expression making possible the insertion of functionally active gene systems into mammalian genomes both in vitro and in vivo. Specifically, the present invention provides a vector capable of expressing homologous and heterologous genes after their introduction into immunoglobulin producing cells, whether in vivo or in vitro, in an integration-site independent cell specific manner.

We have found also that certain of the hypersensitive sites in the mouse λ locus correspond to new useful λ immunoglobulin enhancer elements. Thus the present invention further provides these new enhancer elements and vectors containing these elements, useful for the expression of heterologous genes.

SUMMARY OF THE INVENTION

According to a first aspect of the present invention, there is provided a vector for the integration of a gene into the genetic material of a mammalian host cell such that the gene may be expressed by the host cell, the vector comprising a promoter and the said gene, characterised in that the vector includes an immunoglobulin gene dominant control region capable of eliciting host cell-type restricted, integration site independent, copy number dependent expression of the said gene.

As used herein the term "dominant control region" means a sequence of DNA capable of conferring upon a linked gene expression system the property of host cell-type restricted, integration site independent, copy number dependent expression when integrated into the genome of a host cell compatible with the dominant control region. Such a dominant control region retains this property when fully reconsititued within the chromosome of the host cell. The ability to direct efficient host cell-type restricted expression is retained even when fully reformed in a heterologous chromosomal position.

It is hypothesised that the dominant control regions of the invention may open the chromatin structure of the DNA, making it more accessible and thus may act as a locus organiser.

The dominant control region may be a single contiguous occurring gene system or may consist of two or more such sequences linked together with or without intervening polynucleotides.

The dominant control region may be derived by recombinant DNA techniques from a naturally occurring gene system or may correspond to a naturally occurring gene system in the sense of being manufactured using known techniques of polynucleotide synthesis from sequence data relating to a naturally occurring gene system. Alterations of the sequence may be made which do not alter the function of the dominant control region.

The dominant control region consists of, includes, is derived from, corresponds to, or is associated with, one or more DNase I super hypersensitive sites of an immunoglobulin gene.

The dominant control region may comprise, for example, one or more of the DNase I super hypersensitive sites specifically identified herein.

Other sequences might, however, contribute to or exhibit the functional characteristics of a dominant control region.

A number of DNase super hypersensitive sites have been identified:

i) about 2.4 kb upstream of the CAP site of the rearranged $\lambda_1$ gene, ii) about 2.5 kb upstream of the genomic V$\lambda_2$ segment, and iii) additional sites located at 3' to C$\lambda_1$, and/or C$\lambda_4$ as follows:
about 17 kb 3' of C$\lambda_4$
between 28 and 48 kb (i.e about 30 kb) 3' of C$\lambda_1$ Any of the above-identified super hypersensitive sites may, on their own, constitute a dominant control region or may form part of a dominant control region.

The methods used to identify these super hypersensitive sites may be used to identify functional dominant control regions.

Alternatively functional expression assay methods may be used to identify functional dominant control regions. For example, expression assays using an appropriate reporter gene, such as an immunoglobulin gene may be used, wherein dominant control regions are identified by their capability of eliciting host cell-type restricted, integration site independent, copy number dependent expression of the reporter gene.

Where the naturally occurring dominant control region comprises two or more subsequences separated by an intervening polynucleotides sequence or sequences, the dominant control region may comprise two or more of the subsequences linked in the absence of all or a part of one or more of the intervening sequences. Thus, if the immunoglobulin dominant control region comprises two or more discrete subsequences separated by intervening non-functional sequences, (for example, two or more super hypersensitive sites) the vector of the invention may comprise a dominant control region comprising two or more of the subsequences linked together with all or part of the intervening sequences removed.

One or more super hypersensitive sites may alone or collectively constitute a useful enhancer element derived from the mouse λ immunoglobulin locus.

It will be understood that a super hypersensitive site or a group of such sites which does not exhibit integration site independence is to be considered as an enhancer not a dominant control region.

Enhancers are sequences which activate transcription. They may be located upstream (for example, the SV40 early region enhancer, Banerji et al. 1981 Cell 27:299), downstream (for example the β-globin enhancer, Choi and Engel 1986 Nature 323:731), or within (for example the immunoglobulin heavy chain enhancer, Gillis et al 1983 Cell 33:717, Banerji et al. 1983 Cell 33:729) the transcribed region of the gene.

Enhancers activate transcription in a manner which is relatively independent of their distance from and independent of their orientation with respect to the gene and they are not promoter specific. For example, the immunoglobulin heavy chain enhancer can activate transcription from a β-globin promoter (Picard and Shaffner 1984 Nature 307:80–82).

Some enhancers are active in a variety of different cell types (for example, the enhancers from SV40 and Rous Sarcoma Virus (RSV)). Other enhancers show cell type specificity (for example, the immunoglobulin enhancers are only active in lymphoid cells see Mainatis et al. 1987 Science 236:1237–1245 for a review). This cell-type specificity of enhancer activity can be seen in both cultured cells and transgenic mice (transgenic mice reviewed by Palmiter and Brinster 1986 Ann. Rev. Genet. 20 465–499).

According to a second aspect of the present invention, there is provided a functional enhancer element derived from a mouse λ immunoglobulin locus. The mouse λ immunoglobulin enhancer element may comprise one or more super hypersensitive sites or a separate region within the mouse λ immunoglobulin locus.

The second aspect of the invention includes a vector including an enhancer of the second aspect of the invention. In the case of an expression vector the enhancer is in functional association with a promoter (suitably an immunoglobulin promoter) such that the enhancer activates transcription of a gene downstream of the promoter.

Such an enhancer sequence may contribute to or exhibit the functional characteristics of a dominant control region.

We have identified a region downstream of the mouse C$\lambda_1$ gene segment which possesses enhancer activity and may be a further dominant control region or a part thereof in combination with the super hypersensitive sites of the first aspect of the invention.

The region consists of a DNA sequence comprising all or a functional part of the DNA sequence between the EcoRI site 3.8 kb downstream of the XhoI site in the $C\lambda_1$ gene segment of the rearranged $\lambda_1$ gene and the SnaBI site 10 kb downstream of this XhoI site.

As used herein, the expression "functional" as applied to an enhancer connotes a DNA sequence which is capable of activating transcription from a promoter in a manner which is independent of its distance from or orientation with respect to the gene and is not promoter specific.

As used herein, the expression "downstream" connotes in the direction of transcription.

The mouse immunoglobulin $\lambda_1$ enhancer may be a single contiguous sequence corresponding to, or derived from a naturally occurring mouse immunoglobulin $\lambda_1$ gene system or may consist of two or more such sequences linked together with or without intervening nucleotides or polynucleotides.

The mouse immunoglobulin $\lambda_1$ may be derived by recombinant DNA techniques from a naturally-occurring gene system or may correspond to a naturally occurring gene system in the sense of being manufactured using known techniques of polynucleotide synthesis from sequence data relating to a naturally occurring gene system. Alterations of the sequence may be made which do not alter the function of the mouse immunoglobulin $\lambda_1$ enhancer.

The sequence between the EcoRI site 3.8 kb downstream of the rearranged mouse $\lambda_1$ gene and the SnaBI site 10 kb downstream of the XhoI site in the rearranged mouse $\lambda_1$ gene contains or overlaps two HindIII fragments both of which independently enhance expression of the $\lambda_1$ gene in SP2/0 cells.

The enhancer of the invention may comprise all or a functional part of the 1.3 kb first HindIII to HindIII DNA fragment downstream of the EcoRI site 3.8 kb downstream of the XhoI site in the rearranged mouse $\lambda_1$ gene.

With reference to FIG. 11, the said 1.3 kb HindIII to HindIII fragment downstream of the EcoRI site 3.5 kb downstream of the rearranged mouse $\lambda_1$ gene is that labelled "HIIIA"

The enhancer of the invention may comprise all or a functional part of the 3.3 kb HindIII to HindIII DNA fragment downstream of the EcoRI site 3.8 kb downstream of the XhoI site in the rearranged mouse $\lambda_1$ gene and spanning the SnaBI site 10 kb downstream of the XhoI site in the rearranged mouse $\lambda_1$ gene.

With reference to FIG. 11, the said 3.3 kb HindIII to HindIII fragment downstream of the EcoRI site 3.8 kb downstream of the XhoI site in the rearranged mouse $\lambda_1$ gene and spanning the SnaBI site 10 kb downstream of the XhoI site in the rearranged mouse $\lambda_1$ gene is that labelled "HIIIC".

The term "vector" as used herein connotes in its broadest sense any recombinant DNA material capable of transferring DNA from one cell to another.

The vector may be a single piece of DNA in linear or circular form and may, in addition to the essential functional elements of the invention, include such other sequences as are necessary for particular applications. For example, the vector may contain additional features such as a selectable marker gene or genes, and/or features which assist translation or other aspects of the production of a cloned product.

A vector suitable for integration consists of an isolated DNA sequence comprising an immunoglobulin dominant control region or enhancer and an independent structural gene expression system. The DNA sequence is not linked at either end to other substantial DNA sequences. The isolated DNA sequence may however be provided with linkers for ligation into a vector for replication purposes or may be provided with sequences at one or both ends to assist integration into a genome.

The vector including a dominant control region defines an independent locus which can express homologous and heterologous genes after integration into a mammalian host cell normally capable of immunoglobulin expression, in an integration site independent, copy number dependent manner.

The invention also provides a transfer vector, suitably in the form of a plasmid, comprising an immunoglobulin dominant control region or an enhancer of the second aspect of the invention.

The transfer vector may comprise an isolated functional mouse immunoglobulin $\lambda$ enhancer selected from:

i) the sequence between the EcoRI site 3.8 kb downstream of the XhoI site in the rearranged mouse $\lambda_1$ gene and the SnaBI site 10 kb downstream of the XhoI site in the rearranged mouse $\lambda_1$ gene, ii) all or a functional part of the 1.3 kb first HindIII to HindIII DNA fragment downstream of the EcoRI site 3.8 kb downstream of the XhoI site in the rearranged mouse $\lambda_1$ gene (FIG. 11: that labelled "HIIIA"), iii) all or a functional part of the 3.3 kb HindIII to HindIII DNA fragment downstream of the EcoRI site 3.8 kb downstream of the XhoI site in the rearranged mouse $\lambda_1$ gene and spanning the SnaBI site 10 kb downstream of the XhoI site in the rearranged mouse $\lambda_1$ gene (FIG. 11: that labelled "HIIIC"), The term "gene" as used herein connotes a DNA sequence, preferably a structural gene encoding a polypeptide. The polypeptide may be a commercially useful polypeptide, such as a pharmaceutical, e.g. a plaminogen activator, lymphokine or potentiating or stimulating factor, or an immunoglobulin polypeptide, e.g. a chimeric, humanized or altered immunoglobulin polypeptide. The polypeptide may be entirely heterologous to the host cell. Alternatively, the gene may encode a polypeptide which is deficient absent or mutated in the host cell.

The mammalian host cell may be any mammalian host cell susceptible to uptake of the vector of the invention and capable of immunoglobulin gene expression. The vector DNA may be transferred to the mammalian host cell be transfection, infection, microinjection, cell fusion, or protoplast fusion.

The host cell may be a cell of a living human or an animal. In particular, the host cell may be a cell of a transgenic animal such as a mouse. The host cell may be derived from tissue in which the dominant control region is functional, such as B-cells or precursors thereof (where the dominant control region may not be functional), such as stem cells. The cell may be a lymphoid cell such as a myeloma or hybridoma.

The promoter may be any promoter capable of functioning in the host cell and may be for example a mammalian or viral promoter. Optionally, the promoter may be homologous with the gene locus of the dominant control region and may be present in tandem with another promoter such as a viral tk or other viral promoter and may include one or more enhancer elements. Examples of suitable viral promoters include the SV40 late, Mo MLV LTR, RSV LTR, and hCMV MIE promoters.

The immunoglobulin dominant control region may be from the $\lambda$, $\kappa$ or heavy chain locus or from other genes specifically expressed in B-cells.

In a further aspect of the invention, there is provided a method of producing a polypeptide comprising culturing a host cell transformed with a vector of the invention.

The method may be applied in vitro to produce a desired polypeptide. In addition, the method may be applied in vivo to produce a polypeptide having no therapeutic value to the animal. Such a method of producing a polypeptide is not to be considered as a method of treating the human or animal body.

In a further aspect of the invention the vector may be used in a method of treatment of the human or animal body by replacing or supplementing a defective mammalian gene.

Many diseases of the human or animal body result from deficiencies in the production of certain gene products. The characterising features of the vectors of this invention make them amply suited to the treatment of deficiencies by gene therapy in vivo.

A method of gene therapy is provided comprising removing stem cells from the body of a human or an animal, optionally, killing stem cells remaining in the body, transforming the removed stem cells with a vector of the invention containing a gene deficient, or absent, in the human or animal body, and replacing the transformed stem cells in the human or animal body.

This method can be used to replace or supplement a gene deficient in a human or animal. For example, an individual suffering from adenosine deaminase deficiency, severe combined immune deficiency (SCID) or hgprt deficiency. Thus the method may be used specifically in the treatment of B-cell genetic defects but also in the treatment of general metabolic genetic disorders wherein the cell source of the gene product is not critical.

The invention is now described by way of example with reference to the accompanying drawings.

BRIEF DESCRIPTION OF THE DRAWINGS

FIG. 7(a and b) shows restriction maps of the pLTC cosmid cloning vector (a) and of fragments of J558L DNA cloned at the BamHI site of pLTC. (b) The position of the 7.5 kb EcoRI fragment carrying the $\lambda_1$ gene is shown (all other EcoRI sites have been omitted for clarity). All ApaLI sites mapping 3' of the $\lambda_1$ gene in cos 4N and cos 3'.3 are shown whereas in cos 2B only the ApaLI sites lying further upstream of this site have not yet been mapped.

FIG. 8 shows the results of S1 protection analysis of RNA from various constructs in SP2/0 using a $\lambda_1$ mRNA-specific probe (Lane 1—1 μg J558L RNA: Lane 2—10 μg SP2/0 RNA: Lane 3—10 μg SP2/0-cos2B RNA: Lane 4—10 μg SP2/0-cos4N RNA: Lane 5—10 μg SP2/0-pLTCλ$_1$ RNA: Lane 6—10 μg SP2/0-pSVneoλ$_1$RNA)

T=thymus
S=spleen
L=liver
B=brain

Each track contains 10 μg of RNA hybridised with a 5' $\lambda_1$ cDNA probe and a 5' β actin cDNA problem. 1 μg of J558L RNA was hybridised with the same probes as a positive control.

The position of migration of the protected fragments is indicated by the arrow.

DETAILED DESCRIPTIONS OF EMBODIMENTS

1. Identification of Hypersensitive Sites in J558L Nuclei.

Hypersensitive sites (HSSs) associated with dominant control regions (DCRs) were sought at large distances from the immunoglobulin locus. Southern blots were carried out on myeloma cell-line J558L DNA cut with a variety of 6 base-cutter restriction endocucleases to identify enzymes which generate large fragments carrying the rearranged $\lambda_1$ gene. Two such enzymes were ApaLI and SphI which generated 35 kb and 50 kb fragments carrying the $\lambda_1$ respectively. DNaseI fadeouts were performed on J558L nuclei and DNA extracted from these nuclei was digested with ApaLI or SphI and the fragment pattern was analysed by Southern blotting using a variety of probes. The DNaseI fadeouts were carried out as described by Enver et al (Enver, T. et al., Nature, (1985), 318, 680–683), with the modification described by Grosveld et al (Grosveld F. G. et al., Cell, (1987), 51, 975–985). DNA was prepared from DNaseI-treated nuclei using the procedure of Luster et al. (Luster et al., Mol. Cell Biol., 7, 3723).

Figure 1A:
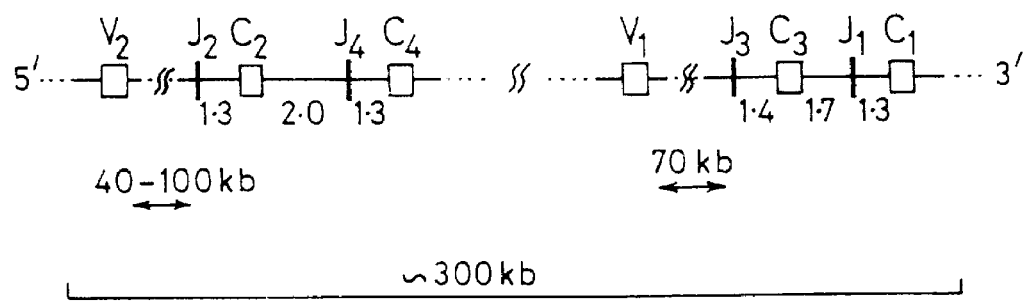
FIG. 1(a-c) shows the structure of mouse immunoglobulin λ, κ and heavy chain loci.
Figure 1B:
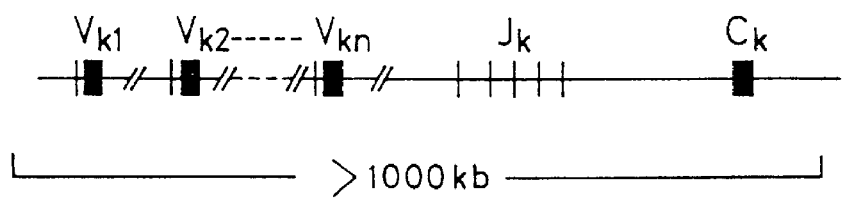
Figure 1C:
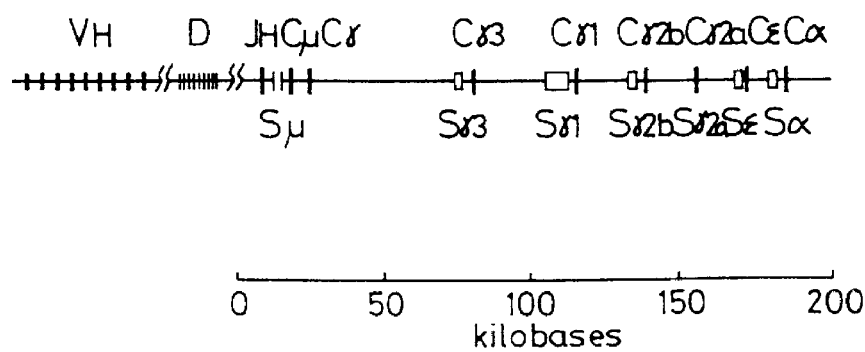
Figure 2:
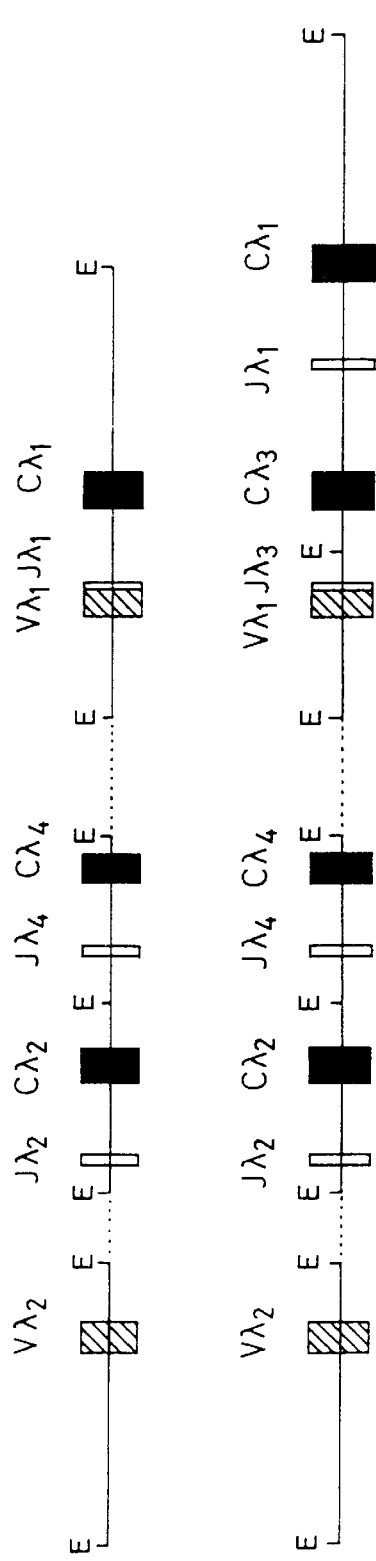
FIG. 2 shows the rearrangements on each mouse chromosome 16 of the λ locus in myeloma cell-line J558L.
Figure 3:
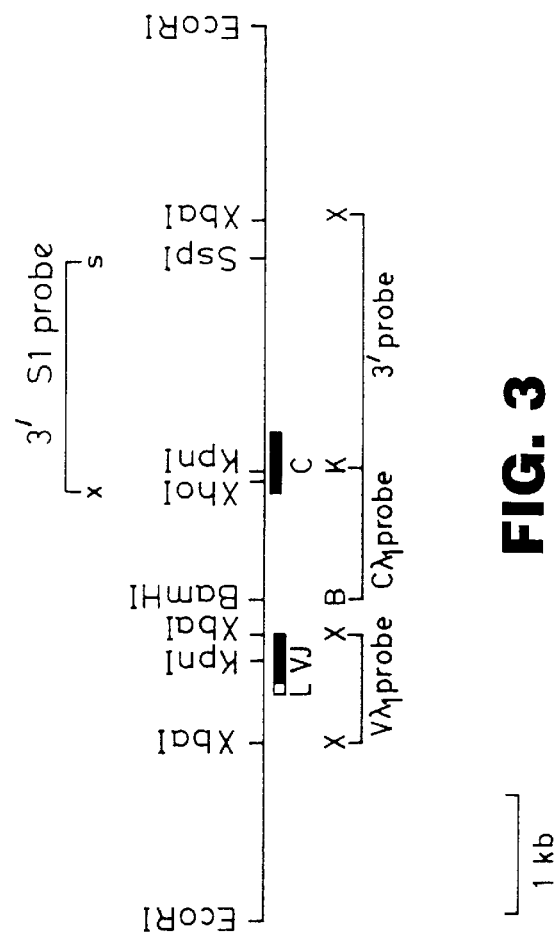
FIG. 3 shows the rearranged mouse $\lambda_1$ gene in the myeloma cell-line J558L.

The probes used were:

1. a probe from the $V\lambda_1$ region (0.8 kb XbaI fragment) which hybridises to both $V\lambda_1$ and $V\lambda_2$ which are highly conserved, 2. a probe from the C region of $\lambda_1$ (1 kb BamHI-KpnI) which hybridises to $C\lambda_1$ and $C\lambda_4$, and 3. a probe from the 3' region of C$\lambda_1$ (2 kb KpnI-XbaI) which is a unique sequence and recognises only C$\lambda_1$-associated sequences (see FIG. 3).

Figure 4A:
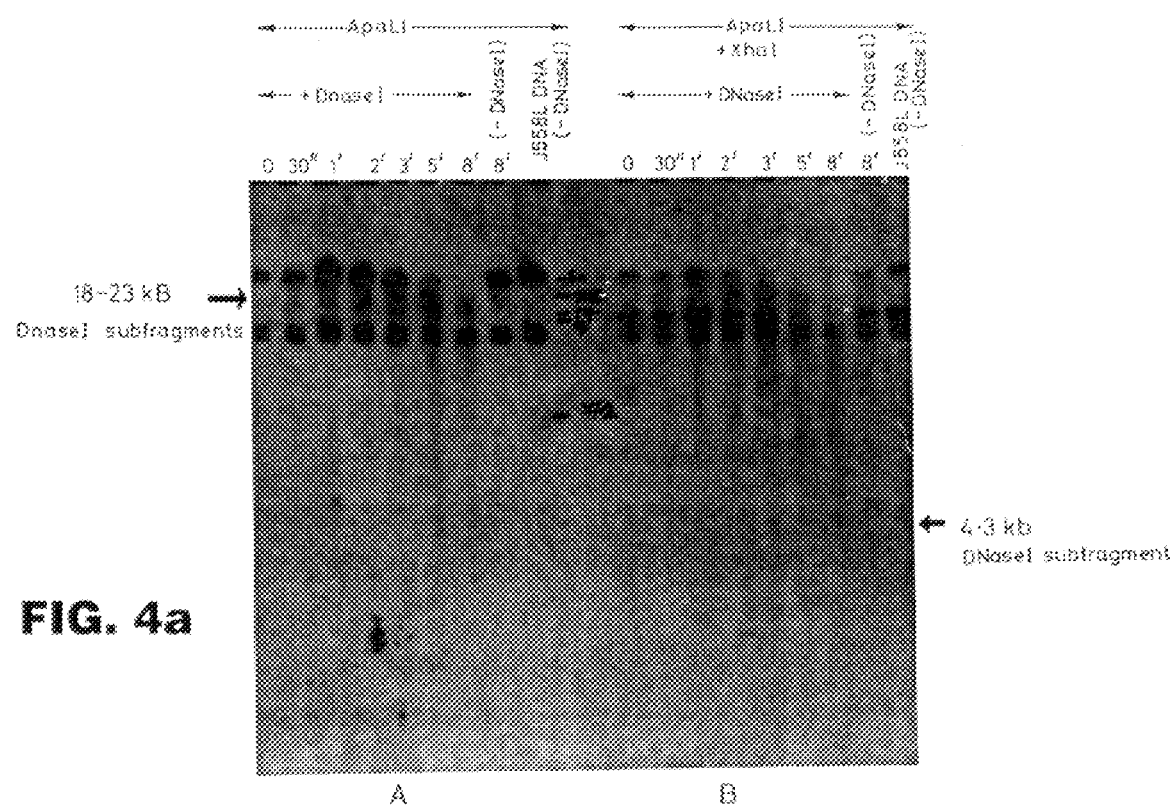
FIG. 4(a and b) shows DNaseI fadeouts on myeloma cell-line J558L muclei cut with a) ApaLI (A) and with ApaLI and XhoI (B), probed with a $C\lambda_1$ probe and b) SphI(A) and with SphI and XhoI(B) probed with a $V\lambda_1$ probe.
Figure 4B:
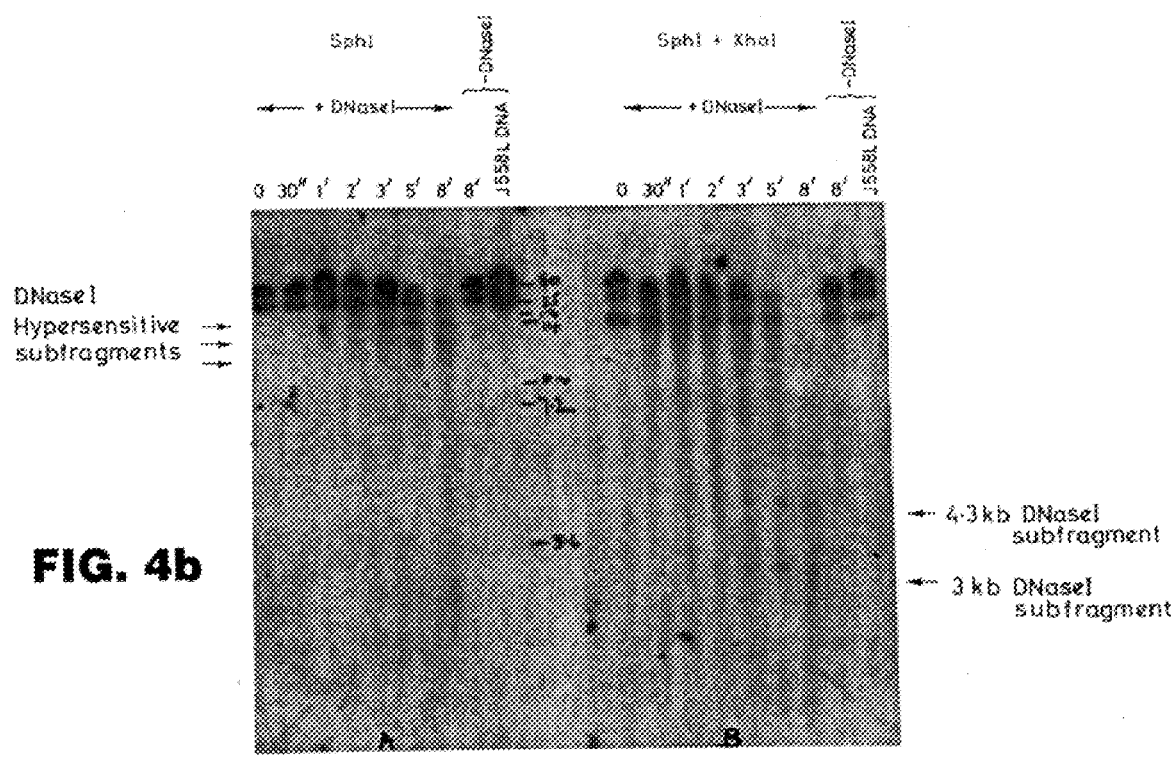

Probling ApaLI or SphI blots with each of these three probes yielded a number of hypersensitive subbands (FIG. 4a and 4b). In order to map these sites more closely, the ApaLI or SphI digested samples were also digested with XhoI (which cuts in the C$\lambda_1$ sequence). A 4.3 kb and a 3 kb band were seen on SphI/XhoI and ApaLI/XhoI blots when probed with the V region probe. The 4.3 kb band was also seen with C$\lambda_1$ probe, showing that the $\lambda_1$ gene contains a hypersensitive site 2.4 kb upstream of the CAP site. The 3 kb subband maps 2.5 kb upstream of the genomic V$\lambda_2$ segment. These positions have been confirmed by mapping with respect to a number of other enzymes (not shown).

In addition to these mapped sites, we have detected a number of other hypersensitive sites using the V, C and 3' probe (FIG. 4a and 4b). All of these are associated with the $\lambda$ locus but cannot be unequivocally assigned to particular positions. What is clear is that some of these are located to the 3' side of the various constant regions.

We therefore decided to clone sequences flanking the $\lambda$ genes to isolate the sequences which contain these hypersensitive sites, starting with the $\lambda_1$ gene.

Figure 5:
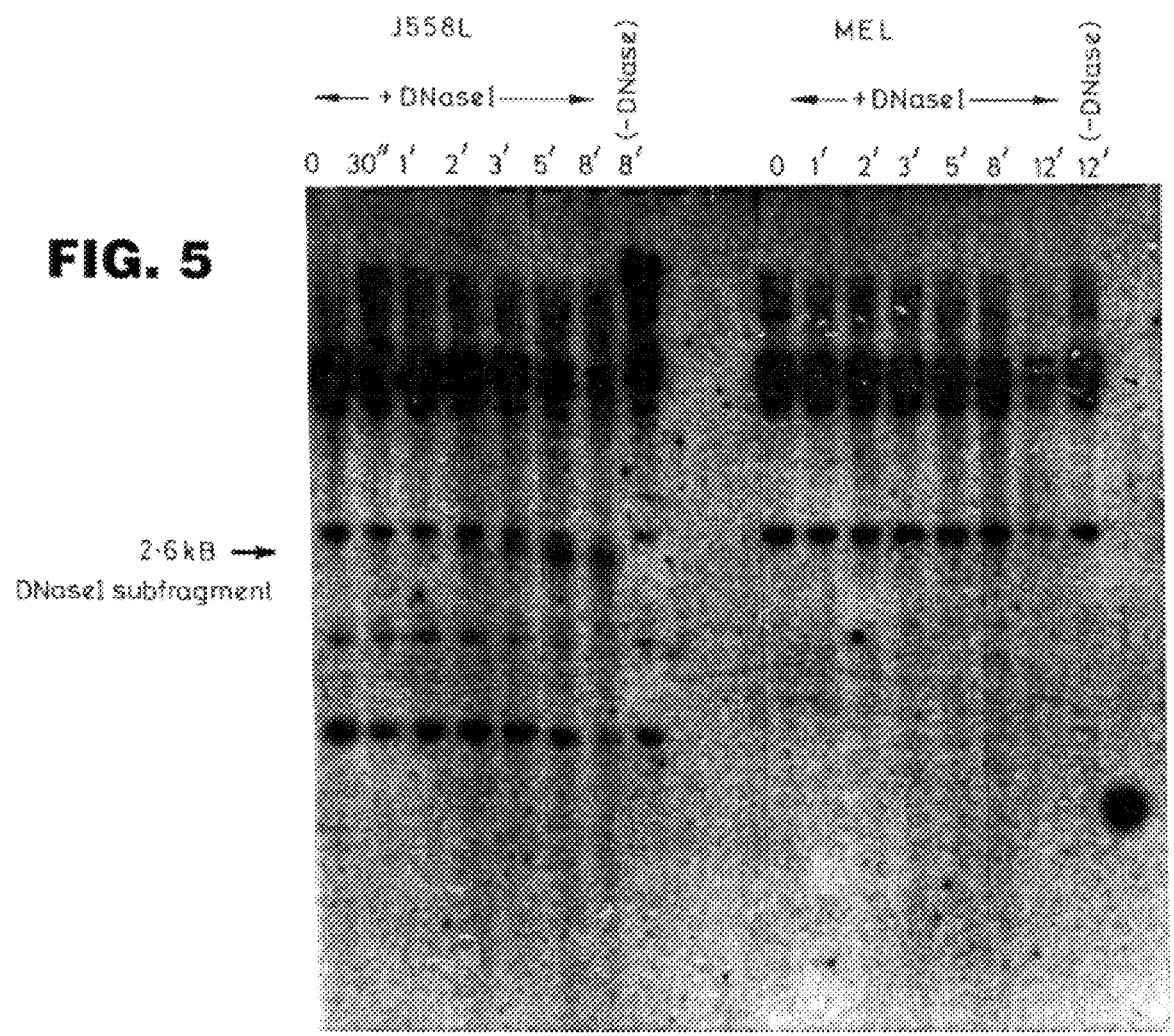
FIG. 5 shows DNaseI fadeouts on nuclei from J558L and MEL nuclei each digested with KpnI and probed with a $V\lambda_1$ probe.
Figure 6:
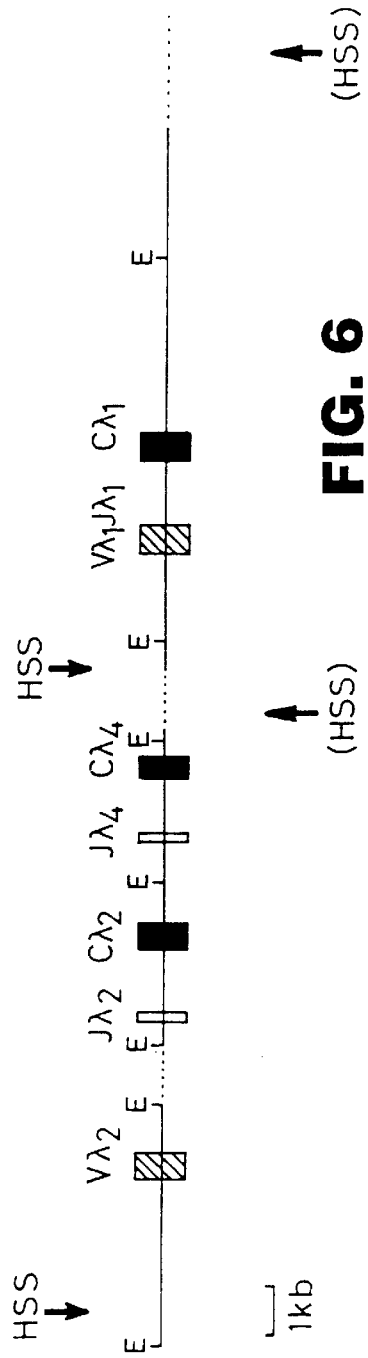
FIG. 6 shows a mapping of the DNaseI hypersensitive sites identified in the J558L genome (3' hypersensitive sites are indicated in parenthesis).

DNaseI fadeouts were performed on nuclei from MEL cells as a control. These were digested with KpnI and probed with a V$\lambda_1$ probe. Whereas hypersensitive bands (2.6 kb) can be seen on the J558L KpnI blots none are seen on the MEL blots (FIG. 5).

2. Construction of a J558L Cosmid Library

In order to clone large fragments flanking the rearranged$\lambda$ gene, a cosmid library was prepared from DNA prepared from J558L cells. A partial MboI digest of J558L DNA was cloned at the BamHI site of the vector pLTC which is identical to pTCF (Grosveld, F. G. et al., NAR, (1982), 10, 6715) except that the HpaI site has been replaced by an XhoI site which was used in place of the HpaI site for the preparation of vector arms.

The cosmid library was prepared using the procedures described by Grosveld et al (Grosveld, F. G et al, NAR, (1982), 10, 6715). Stratagene Gigapack Gold packaging extracts were used according to the manufacturer's instructions and the packaged cosmids were introduced into E. coli MC1061 rec A. The library was plated onto four 20×20 cm NEN Genascreen Plus hybridisation membranes and screened as described by Grosveld et al (Gene, (1981), 13, 227). Hybridisation was carried out using conditions recommended by NEN.

The library (which consisted of 4×10$^6$ individual clones) was screened with the C$\lambda_1$ (1 kb BamHI - KpnI) probe and hybridising colonies were purified. The resulting cosmids were analysed by Southern blotting using V$\lambda_1$ and 3' probes to establish the length of 5' and 3' flanking sequences. Approximately 20 kb of 5' flanking and 20 kb and 3' flanking sequence was isolated in this way. Cos 2B contains the 7.5 kb EcoRI fragment containing the $\lambda_1$ gene and approximately 20 kb of 5' flanking sequence and cos 4N contains the 7.5 kb EcoRI fragment with approximately 20 kb of 3' flanking sequence (FIG. &) including the ApaLI site 3' of the $\lambda_1$ gene.

The library was further screened with a V region probe (0.5 KB SstI V$\lambda_2$ region segment) in order to clone sequences flanking the 5' part of the mouse $\lambda$ locus which may be important in regulating expression.

The library was also screened with a probe from the 3' end of cos4N (an 0.5 kb ApaLI/SalI fragment) in order to clone sequences further 3' of the mouse lambda locus. Cos 3.'.3 was identified with this probe. Cos 3'.3 contains approximately 14 kilobases of sequence overlapping the 3' region of cos4N together with a further 19 kb of 3' sequence. A map of cos 3'.3 is shown in FIG. 7.

3. Functional tests 3.1 Expression myeloma cells.

Cosmids containing the $\lambda_1$ gene and flanking sequences are tested directly by transfection into myeloma cell-lines. The cosmid vector carries a tk-neo gene allowing selection of clones in G418. These are then analysed for expression of the $\lambda_1$ gene by S1 nuclease analysis (for $\lambda_1$ mRNA) and ELISA (for $\lambda_1$ protein). The cosmids are transfected into the cell lines Sp2/0.Ag14 (Shulman et al., Nature, (1978), 276, 269), a mutant hybridoma cell line which produces no antibody, and MOPC 315.26 a heavy chain loss mutant (Hozumi et al., J. Immunol., (1982), 129, 260) which makes $\lambda_2$ light chains.

Sp2/0.Ag14 cells were transfected by electroporation using a Bio-Rad Gene Pulser. 5 µg of linear plasmid DNA was added to 10$^7$ cells in PBS and the cells were shocked at 250 V at a capacitance setting of 960 µF. After the shock, the cells were incubated at room temperature for ten minutes before adding medium (αMEM, 10% Foetal Calf Srum). G418 (1 mg/ml) was added 24 hours after the shock.

S1 mapping was carried out as described by Antoniou et al. (Antoniou, M et al., In: Human Genetic Diseases—A Practical Approach, Ed. Davies, K. E., IRL Press, Oxford).

$\lambda_1$ antibody was measured by ELISA using a goat anti-mouse $\lambda$ light chain specific antibody preparation and a biotinylated derivative of the same (Sourthern Biotechnology). The assay was developed using horseradish peroxidase coupled to avidin and 2,2' azino bis (3-ethylbenzthiazoline-6-sulphonic acid) as substrate.

After testing the effect of 5' flanking sequences (cos 1I and 2B) and 3' sequences alone (cos 4J and 4N), constructs containing both 5' and 3' flanking sequences are prepared by ligation at the XhoI site in the constant region of the $\lambda_1$ gene (FIG. 3).

The levels of expression of all the cosmid constructs can be compared with the level of expression of the 7.5 kb EcoRI fragment containing the $\lambda_1$ gene cloned in the pLTC and with the same fragment cloned in the vector pSVneo which contains an SV40 enhancer. The cell line J558L serves as a positive control for full endogenous expression of $\lambda_1$ mRNA and protein.

pLTC $\lambda_1$ and pSVneo$\lambda_1$ (which both contain the 7.5 kb EcoRI fragment containing the $\lambda_1$ gene) were transfected into Sp2/0.Ag14 cells and populations of G418 resistant clones were analysed for expression of $\lambda_1$ specific mRNA and protein. S1 analysis using a 5' probe from a $\lambda_1$ cDNA cloned in pSPT 18 (Pharmacia) (extending from the SphI site in the vector to the XhoI site in C$\lambda_1$) and protein analysis by ELISA indicated that the populations transfected with pSVneo $\lambda_1$ expressed 100-fold less mRNA and protein than J558L whereas the cells transfected with pLTC $\lambda_1$ did not express detectable levels of mRNA (FIG. 8) or protein (data not shown). This is in agreement with previously reported results. (Picard, D., et al., Nature, (1984), 307, 80–82; Cone, R. D., et al., Science, (1987), 236, 954).

Populations of SP2/0 cells transfected with cos 4N (which contains the $\lambda_1$ gene with 30 kb 3' flanking sequence) also expressed $\lambda_1$ specific messenger RNA, by S1 nuclease analysis (FIG. 8: Lane 4) and synthesised $\lambda_1$ protein, by ELISA.

The level of expression in these populations is similar to, or rather higher than, that seen in populations transfected with pSV neo$\lambda_1$ which contains the SV40 enhancer (FIG. 8: Lane 6).

No expression of $\lambda_1$ specific mRNA or protein could be detected in SP2/0 cells transfected with cos 2B (which contains the $\lambda_1$ gene together with 22 kb of 5' flanking sequence: FIG. 8-Lane 3). This is in spite of the presence in this cosmid of sequences approximately 2.4 kb 5' of the V$\lambda_1$ to which a strong hypersensitive site maps in nuclei treated with DNase I.

All populations which were analysed for mRNA were also checked for the presence of the transfected $\lambda_1$ gene by Southern blotting of EcoRI digested genomic DNA using a probe from the 3' part of the C$\lambda_1$ region (the 2 kb KpnI/XbaI in FIG. 3).

Figure 9:
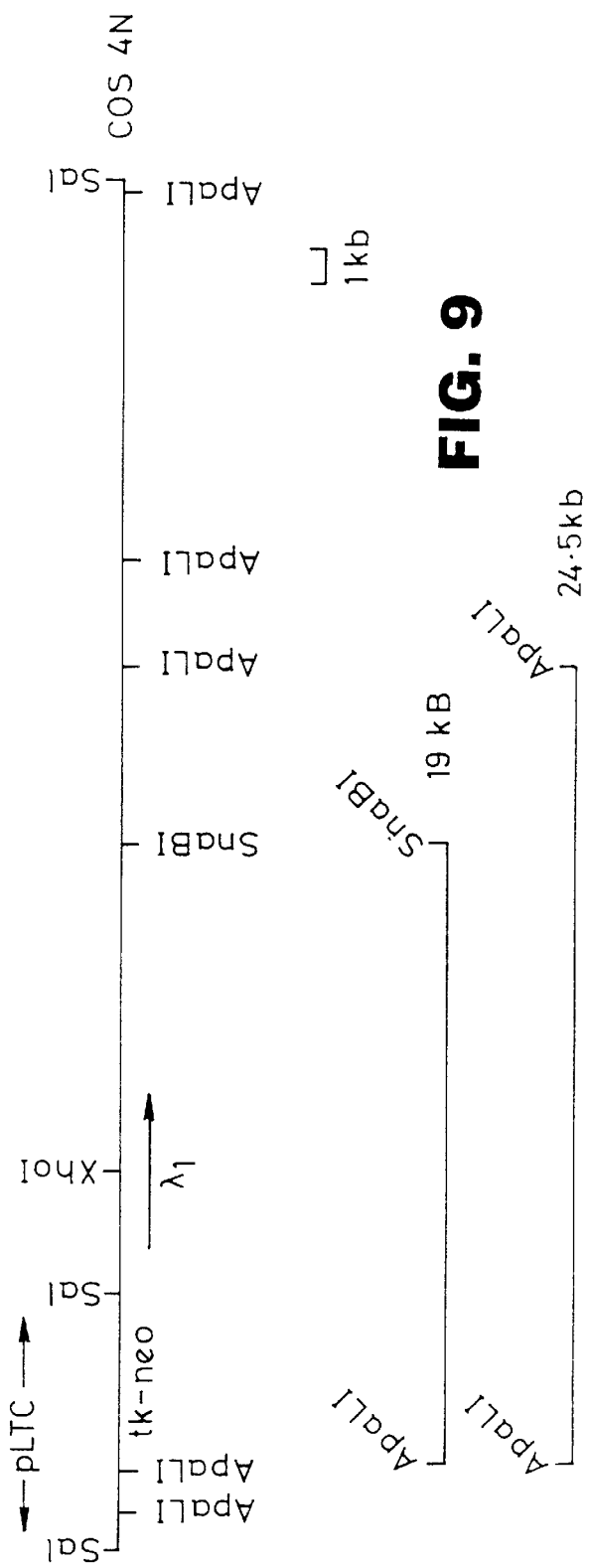
FIG. 9 shows the restriction maps of fragments of cos4N prepared on salt gradients and used to transfect SP2/0.
Figure 10:
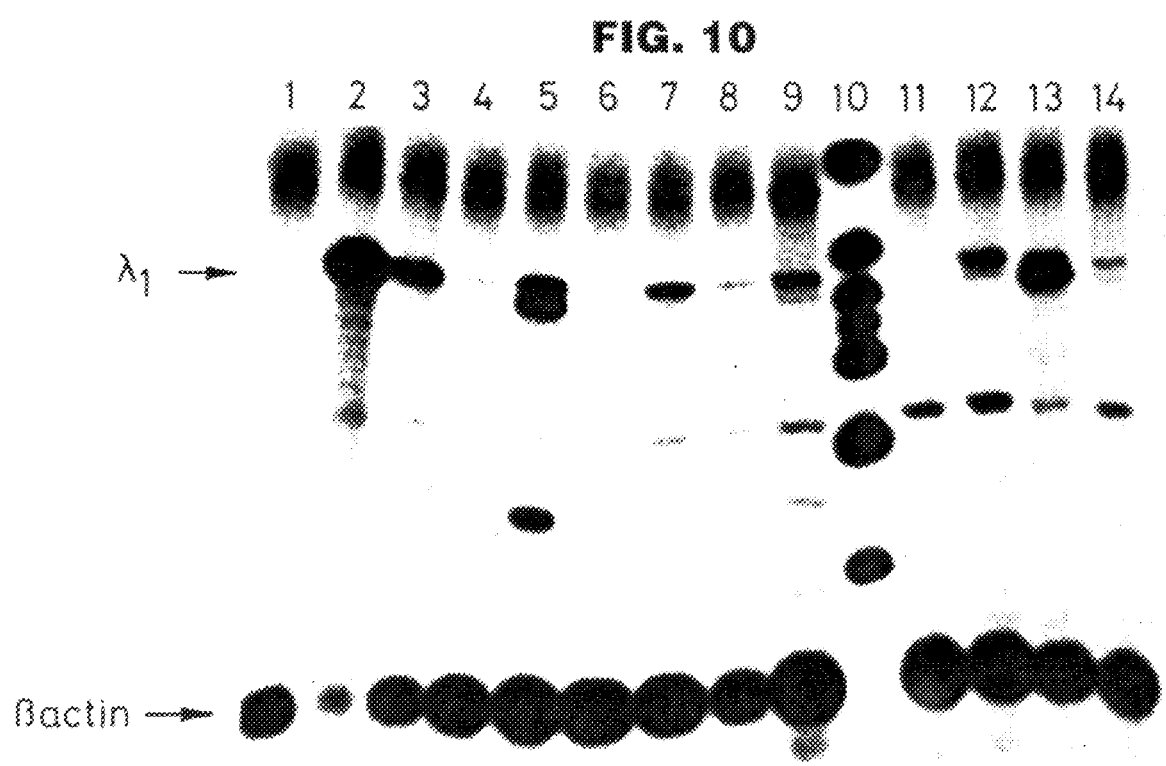
FIG. 10 shows the results of S1 protection analysis on RNA from the fragments shown in FIG. 9 in SP2/0 using a $\lambda_1$ mRNA-specific probe (Lane 1—10 μg SP2/0 RNA: Lane 2—10 μg J558L RNA: Lanes 3 and 4—10 μg SP2/0-cos4N RNA: Lanes 5 to 9—10 μg SP2/0-cos4N ApaLI 24.5 kb fragment RNA: Lane 10 - pBR322 HinfI markers: Lanes 11 to 14—10 μg SP2/0-cos4N ApaLI/SnaBI19 kb fragment RNA)

In order to determine how much of the 3' sequence in cos 4N was necessary for expression of the $\lambda_1$, restriction fragments of cos 4N containing the tk-neo gene, the $\lambda_1$ gene and various amounts of 3' sequence were prepared on salt gradients and used to transfect SP2/0 cells. Populations of clones resistant to G418 were tested for expression of the $\lambda_1$ gene by S1 nuclease protection. These fragments are shown in FIG. 9. Both the 24.5 kb ApaLI fragment and the 19 kb ApaLI-SnaBI fragment gave populations of SP2/0 cells which expressed $\lambda_1$ specific nRNA (FIG. 10: Lanes 5 to 9 and 11 to 14).

Figure 11:
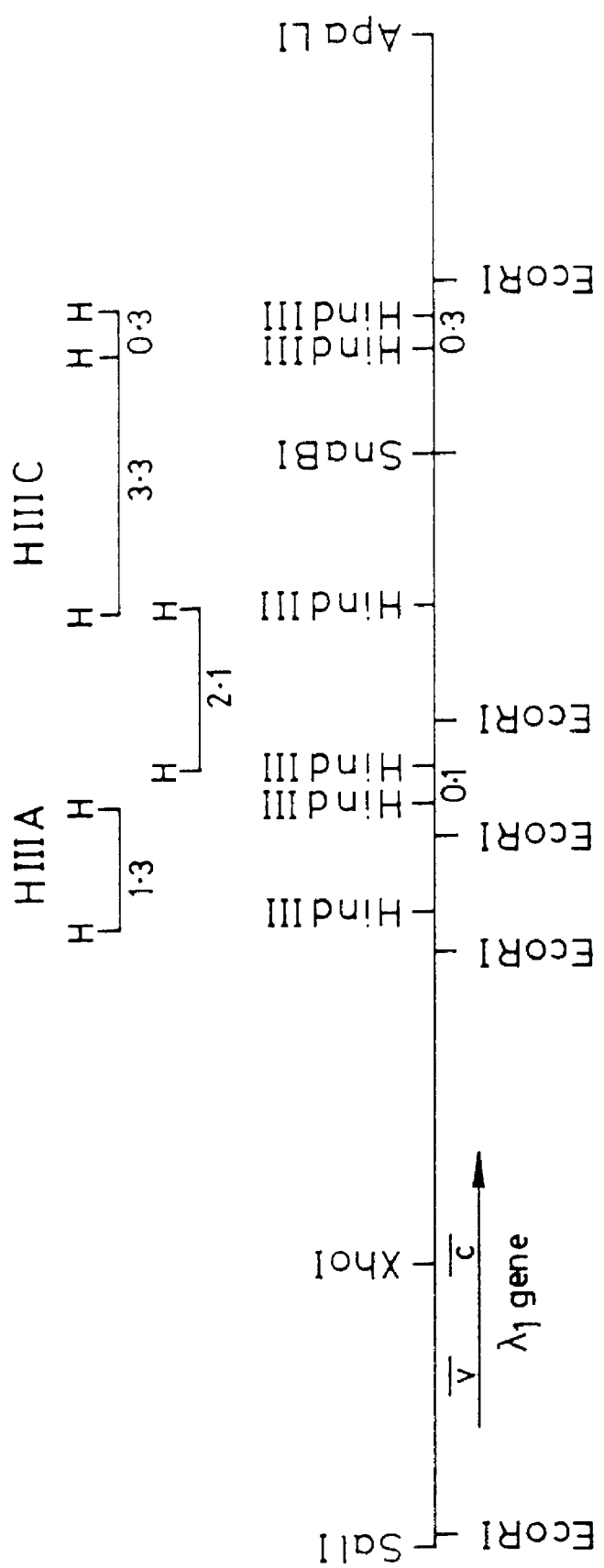
FIG. 11 shows the restriction map of the enhancer region of the mouse $\lambda_1$ gene including the two HindIII fragments thereof which exhibit enhancer activity.
Figure 12:
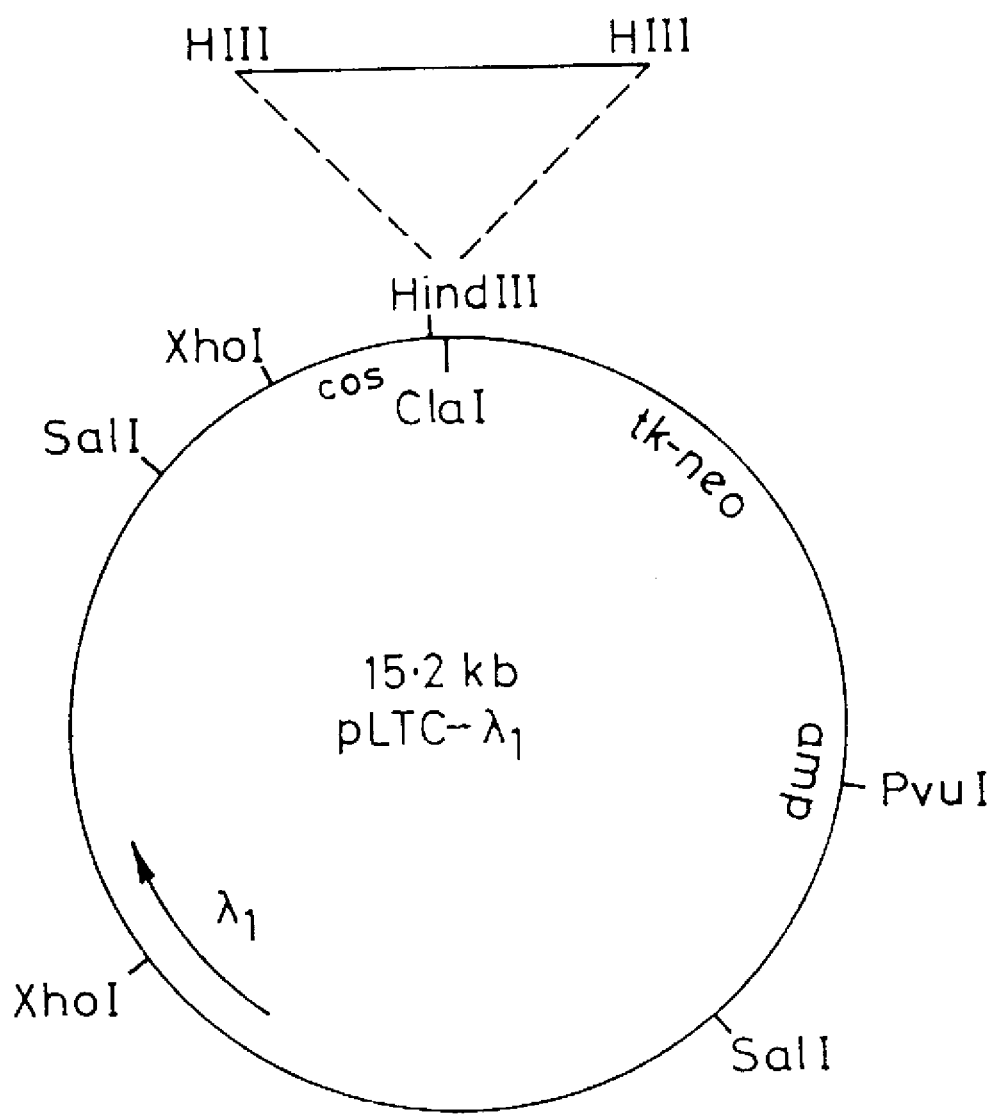
FIG. 12 shows the restriction maps of the plasmid, pLTCλ$_1$, used to test putative enhancer fragments for transcription activation by stable transfection of SP2/0.

HindIII fragments lying between the EcoRI site 3.8 kb downstream of the XhoI site in the $\lambda_1$ gene and the SnaBI site 10 kb downstream of this XhoI site (FIG. 11) were cloned into the HindIII site of pLTC$\lambda_1$ (FIG. 12). These plasmids were linearised at the single PvuI site and used to transfect SP2/0 cells.

Figure 13:
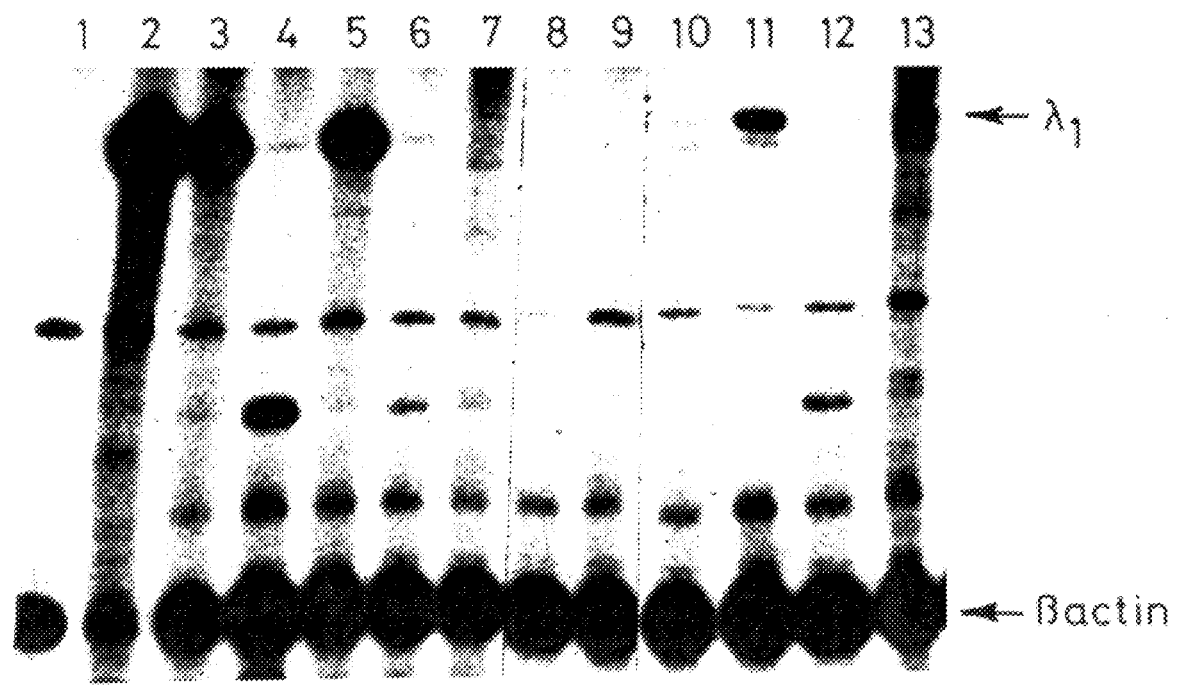
FIG. 13 shows the results of S1 protection analysis on RNA from the vectors shown generally in FIG. 12 (a) in SP2/0 using a $\lambda_1$ mRNA-specific probe (Lane 1—10 μg SP2/0 RNA: Lane 2—1 μg J558L RNA: Lane 3–10 μg SP2/0-cos4N RNA: Lanes 4 and 5 - SP2/0 pLTCλ1HIIIAα 10 μg RNA: Lanes 6 and 7 - SP2/0 pLTCλ$_1$ HIIIAβ 10 μg RNA: Lanes 8 and 9 - SP2/0 pLTCλ$_1$ 10 μg RNA: Lanes 10 and 11 - SP2/0 pLTCλ$_1$ HIIICα 10 μg RNA: Lanes 12 and 13 - SP2/0 pLTCλ$_1$ HIIICβ 10 μg RNA).

RNA from CT418 resistant populations was tested for the presence of $\lambda_1$ specific mRNA as before. A plasmid containing the 1.3 kb HindIII fragment, HIIIA, expressed $\lambda_1$ mRNA as did plasmids containing the 3.3. kb HindIII fragment HIIIC (FIG. 13; Lanes 4 to 7 and 10 to 14).

In conclusion, an enhancer downstream of the mouse C$\lambda_1$ gene segment has been identified. Enhancer activity lies between the EcoRI site 3.8 kb downstream of the XhoI site in the $\lambda_1$ gene and the SnaBI site 10 kb downstream of this XhoI site. This region contains two Hind III fragments (HIIIA 1.3 k$\beta$ and HIIIC 3.3 kb) both of which enhance expression of the $\lambda_1$ gene in SP2/0 cells.

3.2 Transgenic Mice.

The SalI fragments of cos 4N and cos 3+.3 which contains all the cloned J558L DNA were purified using salt gradients. The cos 4 N SalI fragment was injected into fertilized mouse eggs (C57BL/10×CBA) FI, either alone or as a co-injection with the SalI fragment of cos 3'.3 in order to generate transgenic mice containing the $\lambda_1$ gene together with varying amounts of 3' flanking sequence. The expression of the $\lambda_1$ gene in these mice was monitored both by S1 nuclease protection analysis of mRNA from lymphoid and non-lymphoid tissues and by fluorescence activated cell sorter analysis of $\lambda_1$ protein expression on the surface of spleen cells.

Two mouse lines were generated which carried both cos 4N and cos 3'.3 SalI fragments in their genome. Southern blot analysis using probes from the ends of the SalI fragments indicated that the cos 4N and cos 3.40 .3 fragments were linked together at the same insertion site in the genome (data not shown).

The founder animals were bred with (C57BL/10×CBA) FI mice and their offspring analysed 5–7 days after birth for expression of $\lambda_1$. RNA prepared from spleen, liver, thymus and brain was analysed by S1 nuclease protection using a probe from the 5' end of $\lambda_1$ cDNA. For analysis of cell surface expression of $\lambda_1$, spleen tissue was homogenised using a glass homogeniser and red cells were lysed using Tris-ammonium chloride. Approximately $10^6$ cells were stained with phycoerythrin conjugated goat anti-mouse $\lambda$ (Southern Biotechnology) or fluorescein isothiocyanate conjugated goat anti-mouse $\mu$ (Sigma). Fluorescence analysis was carried out using a Beckman Dickinson FACSTAR-PLUS flow cytometer. Transgenic animals were identified by Southern blotting of tail DNA using probes from both cos 4N and cos 3'.3.

Figure 14:
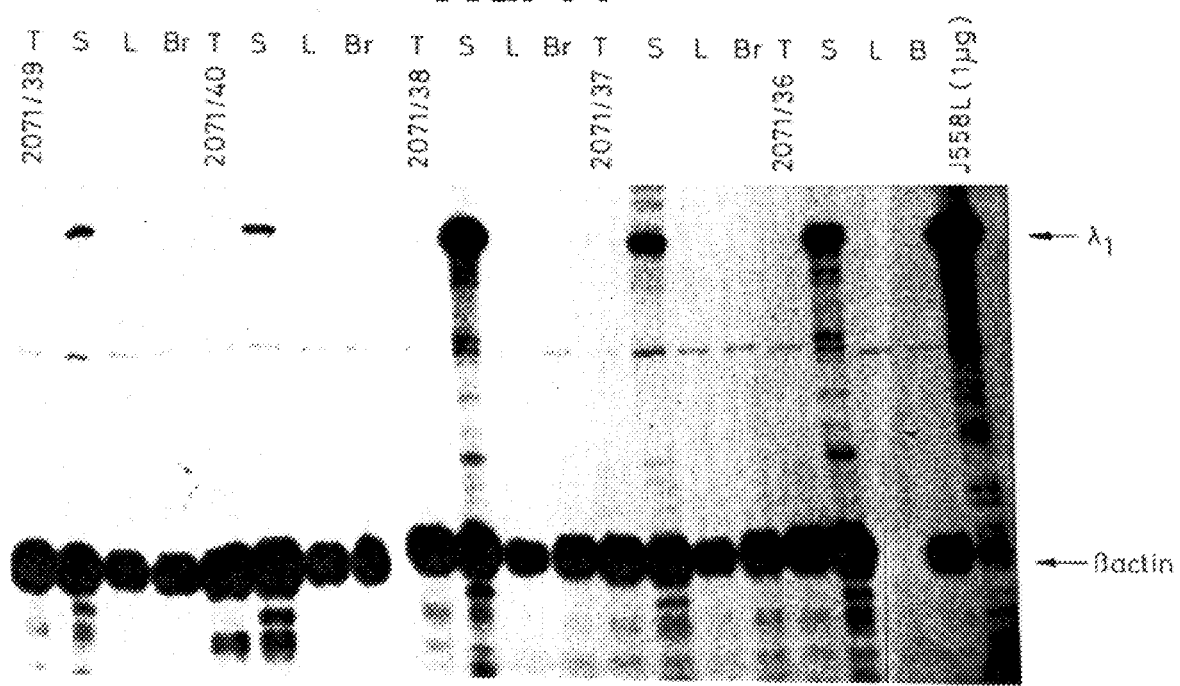
FIG. 14 shows S1 nuclease protection analysis of mRNA from tissues of transgenic (36, 37 and 38) and non-transgenic (39 and 40) littermats of the mouse line 2071.

For the two mouse lines, 2071 and 3002, the transgenic offspring exhibited an elevation in both the number of spleen cells expressing lambda chains at the cell surface and in the level of $\lambda_1$ mRNA detected in the spleen compared with non-transgenic littermates. FIG. 14 shows an S1 nuclease protection analysis of RNA from various tissues of two non-transgenic and three transgenic off spring of line 2071. The three transgenic offspring shown an approximately 5–10 fold increase in the level of $\lambda_1$ specific RNA in the spleen and no detectable expression in thymus, brain or liver. Similar results were obtained for mouse line 3002. Table 1 shows the results of FACS analysis of spleen cells from 5 day old offspring of lines 2071 and 3002. In both cases the number of 1 gM positive B cells expressing lambda chains was approximately 5 fold higher in the transgenic animals compared with their non-transgenic littermates.

TABLE 1

FACS analysis of spleen cells from transgenic and non-transgenic littermates of mouse lines 2071 and 3002.

| Mouse | Transgene cos 4N | Transgene cos 3'.3 | % spleen cells staining with PE-GAM λ | FITE-GAM μ | % λ/μ |
|---|---|---|---|---|---|
| 2071/21 | X | X | 5.0, 5.0 | 15.5, 14.6 | 33 |
| 2071/22 | X | X | 3.7, 3.3 | 13.6, 12.7 | 27 |
| 2071/23 | X | X | 1.4, 1.4 | 20.9, 19.4 | 7 |
| 2071/24 | — | — | 1.1, 1.0 | 14.3, 15.5 | 6 |
| 3002/1 | X | X | 4.57, 4.34 | 7.89, 9.96 | 50 |
| 3002/2 | X | X | 3.32, 2.54 | 6.56, 6.43 | 45 |
| 3002/3 | X | X | 0.39, 0.52 | 6.16, 5.87 | 7.5 |
| 3002/4 | X | X | 0.39, 0.40 | 4.33, 5.16 | 8.3 |
| 3002/5 | X | X | 2.87, 2.97 | 7.62, 7.64 | 38 |
| 3002/6 | X | X | 2.36, 2.91 | 6.43, 6.81 | 40 |

Six mouse lines carrying various numbers of copies of the cos 4N SalI fragment alone were also analysed. No difference was observed either in the number of $\lambda$ expressing B cells or in the level of $\lambda_1$ specific mRNA in the spleen between transgenic and non-transgenic offspring.

We concluded from these data that an element which strongly enhances the expression of the mouse $\lambda_1$ gene resides in the sequences towards the 3' end of cos 4'.3 The presence of DNaseI hypersensitive sites in this region was investigated by digesting DNA from a DNaseI fadeout of J558L nuclei with the enzymes XhoI and PvuI and probing Southern blots with a 1.9 kb EcoRV-PvuI fragment from the 3' end of cos 3.40 .3. The probe hybridises to a 28 kb fragment in J558L DNA. Preliminary data suggest that there may be two hypersensitive sites mapping approximately 8 kb and 12 kb upstream of the PvuI site. J558L fadeouts were also digested with ApaLI and Southern blots probed with a 1 kb EcoRI/SnaBI fragment from cos 3'.3 (see FIG. 7b). Preliminary exposures of these blots suggest the appearance of a DNaseI hypersensitive subband approximately 5 kb downstream of the most 3' ApaLI site in cos 3'.3. These may therefore be 2 or 3 DNaseI hypersensitive sites which map to the region lying between 28 and 48 kb (i.e. about 30 kb) downstream of the XhoI site in the rearranged $\lambda_1$ gene.

Both the mouse lines 3002 and 2071 contain between five and eight copies of each of the cos 4 N and cos 3'.3 SalI fragments. Since approximately five times the number of B cells are expressing $\lambda_1$ chains as in the non-transgenic animals and the level of $\lambda_1$ specific RNA is increased between 5 and 10 fold, the level of expression of the transgene appears to be approaching the level of expression of an endogenous $\lambda_1$ allele. The generation of more mouse lines containing sequences from cos 4N and cos 3'.3 will confirm whether expression levels are directly correlated with copy number.

The data are consistent with the sequences from cos 3'.3 to which the hypersensitive site maps acting as a DCR. They are, in any case, acting as a strong, B cell specific enhancer. Possibly addition of 5' sequences containing the hypersensitive site kb upstream of the CAP site of the rearranged $\lambda_1$ gene to the injected DNA may complete a functional DCR.

A variation on this approach to isolating DCR's involves using very large segments of the mouse lambda locus cloned in yeast artificial chromosomes (YACS) (Murray and Szostak, 1983, Nature 305:189–193). Several hundred kilobases of DNA can be cloned using YAC vectors. A YAC library prepared from J558L DNA would be screened for clones containing lambda sequences. These clones would be tested for expression of lambda either by transfection into myeloma cells or by injection info fertilised mouse eggs. Copy number dependent, tissue specific, high level expression would be indicative of the presence of a DCR and sequences responsible for this could be identified by DNaseI hypersensitive site mapping. These could then be subcloned from the YAC clone.

The present invention identifies, for the first time, sequences for dominant control regions associated with the mouse $\lambda$ immunoglobulins locus.

In the cell line J558L, which synthesises $\lambda_1$ light chains, hypersensitive sites have been identified 2.3~2.4 kb upstream of the CAP site of the rearranged $\lambda_1$ gene, 2.5 kb upstream of the genomic $V\lambda_2$ segment approximately 30 kb 3' of the rearranged $\lambda_1$ gene and approximately 17 kb 3' of the $C\lambda_4$ gene segment. Sequences to which these sites map have been cloned from the J558L cell-line and their effect on $\lambda_1$ gene expression tested in myeloma cells and transgenic mice.

The DNaseI hypersensitive sites described here may represent "super" hypersensitive sites since non "normal" hypersensitive sites were detected associated with the $\lambda_1$ immunoglobulin promoter. It is possible that the DNaseI hypersensitive sites are "super" hypersensitive because they comprise a cluster of hypersensitive sites, for example as has been shown for the β-globin locus. The location of the hypersensitive sites is also consistent with the probable location of DCRs by analogy with the β-globin and CD2 loci (i.e. 5' and 3' of the locus).

It will be understood that the invention is described by way of example only and modifications of detail may be made within the scope of the invention.

We claim:

1. In a method of obtaining production of a gene product in a mammalian host cell which permits immunoglobulin gene expression, the improvement comprising introducing into said host cell a recombinant DNA comprising (I) a dominant control region that is functional in a mammalian cell-type which permits immunoglobulin gene expression, (ii) a promoter that is functional in said mammalian cell-type, and (iii) a gene encoding said gene product operatively linked to said promoter, wherein the region in said DNA consisting of (I), (ii) and (iii) and DNA therebetween as a nucleotide sequence different from that of naturally occurring DNA, and said dominant control region being characterized in that in naturally occurring DNA:

(I) it is associated with a naturally occurring immunoglobulin gene locus; and (II) it is locatable in naturally occurring DNA by association with a DNase I super hypersensitive site;

wherein said dominant control region is characterised in that it stimulates expression of said gene when said DNA molecule is integrated into a genome of a host cell which permits expression of said naturally occurring immunoglobulin gene locus, such that said expression:

(a) is independent on the number of copies of said gene that are integrated into said genome in that said expression increases as said number of copies o said gene increases; and (b) is independent of the integration site of said DNA molecule in said genome.

2. In the method of claim 1, the improvement comprising introducing said recombinant DNA into said host cell in a mammal.

3. In the method of claim 1, the improvement comprising transfecting said host cell ex vivo with said recombinant DNA.

4. In the method of claim 1, the improvement wherein the dominant control region is a dominant control region of the mouse $\lambda$ immunoglobulin gene locus.

5. In the method of claim 1, the improvement wherein said dominant control region comprises a DNAse I super hypersensitive site which is upstream of an immunoglobulin V region gene segment and a DNAse I super hypersensitive site which is downstream of an immunoglobulin C region gene segment.

6. In the method of claim 4, the improvement wherein the dominant control region is associated with a DNase I super hypersensitive site which is about 2.3 kb upstream of the CAP site of the rearranged $\lambda_1$ gene.

7. In the method of claim 4, the improvement wherein the dominant control region is associated with a DNase I super hypersensitive site which is about 2.5 kb upstream of the unrearranged $V\lambda_2$ segment.

8. In the method of claim 4, the improvement wherein the dominant control region is associated with a DNase I super hypersensitive site which is about 30 kb downstream of the rearranged $\lambda_1$ gene.

9. In the method of claim 4, the improvement wherein the dominant control region is associated with a DNase I super hypersensitive site which is about 17 kb downstream of the $C\lambda_4$ gene segment.

10. In the method of claim 5, the improvement wherein said dominant control region is associated with a DNase I super hypersensitive site which is upstream of a $V\lambda$ gene segment and a DNase I super hypersensitive site which is downstream of a $C\lambda$ gene segment.

11. In the method of claim 5, the improvement wherein said dominant control region is associated with a DNase I super hypersensitive site which is about 2.3 kb upstream of the CAP site of the rearranged $\lambda_1$ gene and a DNase I super hypersensitive site which is about 30 kb downstream of the rearranged $\lambda_1$ gene.

* * * * *